(12) United States Patent
Roseboom et al.

(10) Patent No.: US 7,122,650 B2
(45) Date of Patent: Oct. 17, 2006

(54) PROMOTER SEQUENCES FOR CORTICOTROPIN RELEASING-FACTOR BINDING PROTEIN AND USE THEREOF

(75) Inventors: Patrick H. Roseboom, Madison, WI (US); Ned H. Kalin, Madison, WI (US); Steven A. Nanda, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 414 days.

(21) Appl. No.: 10/676,526

(22) Filed: Oct. 1, 2003

(65) Prior Publication Data

US 2004/0132065 A1 Jul. 8, 2004

Related U.S. Application Data

(60) Provisional application No. 60/415,586, filed on Oct. 2, 2002.

(51) Int. Cl.
*C07B 21/04* (2006.01)
*C12Q 1/68* (2006.01)
*C12N 1/00* (2006.01)
*C12N 15/00* (2006.01)
*C12N 15/09* (2006.01)

(52) U.S. Cl. .................. 536/23.4; 435/320.1; 435/6; 514/44

(58) Field of Classification Search ............... 536/23.4; 435/320.1, 6; 514/44
See application file for complete search history.

(56) References Cited

U.S. PATENT DOCUMENTS 6,023,011 A 2/2000 Vale, Jr. et al.

OTHER PUBLICATIONS

Accession No. S60697, 1993.*
Cortright et al. Isolation and Characterization of the Rat Corticotropin releasin hormone (CRH)–binding protein gene: Transcriptional Regulation by Cyclic Adenosine Monophosphate and CRH Endocrinology 138(5) 1997 2098–2108.*
Aborelius L, Owens MJ, Plotsky PM, Nemeroff CB (1999) The role of corticotropin–releasing factor in depression and anxiety disorders. J Endocrinol 160:1–12.
Baker DG, West SA, Nicholson WE, Ekhator NN, Kasckow JW, Hill KK, Bruce AB, Orth DN, Geracioti TD, Jr. (1999) Serial CSF corticotropin–releasing hormone levels and adrenocortical activity in combat veterans with posttraumatic stress disorder. Am J Psychiatry 156:585–588.
Bakshi VP, Smith–Roe S, Newman SM, Grigoriadis DE, Kalin NH (2002) Reduction of stress–induced behavior by antagonism of corticotropin–releasing hormone 2 (CRF2) receptors in lateral septum or CRF1 receptors in amygdala. J Neurosci 22:2926–2935.

Beglinger C, Degen L (2002) Role of thyrotropin releasing hormone and corticotrophin releasing factor in stress related alterations of gastrointestinal motor function. Gut 51 Suppl 1:I45–I49.
Behan DP, De Souza EB, Lowry PJ, Potter E, Sawchenko P, Vale WW (1995) Corticotropin releasing factor (CRF) BP: a novel regulator of CRF and related peptides. Front Neuroendocrinol 16:362–382.
Behan DP, Khongsaly O, Owens JJ, Chung HD, Nemeroff CB, DeSouza EG (1997) Corticotropin–Releasing Factor (CRF), CRF–BP (CRF–BP), and CRF/CRF–BP Complex in Alzheimer's Disease and Control Postmortem Human Brain, Journal of Neurochemistry 68:2053–2060.
Bremner JD, Licinio J, Darnell A, Krystal JH, Owens MJ, Southwick SM, Nemeroff CB, Charney DS (1997) Elevated CSF corticotropin–releasing factor concentrations in post-traumatic stress disorder. Am J Psychiatry 154:624–629.
Chappell P, Leckmen J, Goodman W, Bissette G, Pauls D, Anderson G, Riddle M, Scahill L, McDougle C, Cohen D (1996) Elevated cerebrospinal fluid corticotropin–releasing factor in Tourette's syndrome: comparison to obsessive compulsive disorder and normal controls. Biol. Psychiatry 39:776–783.
Chen R, Lewis KA, Perrin MH, Vale WW (1993) Expression cloning of a human corticotropin–releasing–factor receptor. Proc Natl Acad Sci U S A 90:8967–8971.
Cortright D, Goosens K, Lesh J, Seasholtz A (1997) Isolation and characterization of the rat corticotropin–releasing hormone (CRF) BP gene: Transcriptional regulation by cyclic adenosine monophosphate and CRF. Endocrinology 138:2098–2108.
Coste SC, Quintos RF, Stenzel–Poore MP (2002) Corticotropin–releasing hormone–related peptides and receptors. Emergent regulators of cardiovascular adaptations to stress. Trends Cardiovasc Med 12:176–182.
Fossey MD, Lydiard RB, Ballenger JC, Laraia MT, Bissette G, Nemeroff CB (1996) Cerebrospinal fluid corticotropin–releasing factor concentrations in patients with anxiety disorders and normal comparison subjects. Biol Psychiatry 39:703–707.
Gasparotto OC, Ignacio ZM, Lin K, Goncalves S (2002) The effect of different psychological profiles and timings of stress exposure on humoral immune response. Physiol Behav 76:321–326.

(Continued)

*Primary Examiner*—James Ketter
*Assistant Examiner*—Konstantina Katcheves
(74) *Attorney, Agent, or Firm*—Quarles & Brady LLP (57) ABSTRACT

Various human corticotropin-releasing factor binding protein promoter sequences are disclosed. Nucleic acids and host cells that contain the promoter sequences are also disclosed. Further disclosed are various methods involving the use of these sequences.

14 Claims, 5 Drawing Sheets

OTHER PUBLICATIONS

Guillemin R, Rosenberg B (1955) Humoral hypothalamic control of anterior pituitary: a study with combined tissue cultures. Endocrinology 57:599–607.

Kostich Wa, Chen A, Sperle K, Largent BL (1998) Molecular identification and analysis of a novel human corticotropin– releasing factor (CRF) receptor: the CRF2gamma receptor [In Process Citation]. Mol Endocrinol 12:1077–1085.

Lewis K, Li C, Perrin MH, Blount A, Kunitake K, Donaldson C, Vaughan J, Reyes TM, Gulyas J, Fischer W, Biliezikjian L, Rivier J, Sawchenko PE, Vale WW (2001) Identification of urocortin III, an additional member of the corticotropin–releasing factor (CRF) family with high affinity for the CRF2 receptor. Proc Natl Acad Sci U S A 98:7570–7575.

Linton, EA, Behan DP, Saphier PW, Lowry PJ (1990) Corticotropin–Releasing Hormone (CRF)–BP: Reduction in the Adrenocorticotropin–Releasing Activity of Placental but not Hypothalamic CRF, Journal of Endocrinology and Metabolism 70: 1574–1580.

Lovenberg TW, Liaw CW, Grigoriadis DE, Clevenger w, Chalmers DT, De Souza EB, Ottersdorf T (1995) Cloning and characterization of a functionally distinct corticotropin-releasing factor receptor subtype from rat brain [published erratum appears in Proc Natl Acad Sci U S A Jun. 6, 1995;92(12);5759]. Proc Natl Acad Sci U S A 92:836–840.

McGaugh JL, Roozendaal B (2002) Role of adrenal stress hormones in forming lasting memories in the brain. Curr Opin Neurobiol 12:205–210.

Mitchell AJ (1998) The role of corticotropin in releasing factor in depressive illness: a critical review. Neurosci Biobehav Rev 22:635–651.

Nemeroff CB (1989) Clinical Significance of Psychoneuroendocrinology in Psychiatry: Focus on the Thyroid and Adrenal. J Clin Psychiatry 50:13–20.

Perrin M, Donaldson C, Chen R, Blount A, Berggren T, Bilezikjian L, Sawchenko P, Vale W (1995) Identification of a second corticotropin–releasing factor receptor gene and characterization of a cDNA expressed in heart. Proc Natl Acad Sci USA 92:2969–2973.

Potter E, Behan DP, Fischer WH, Linton EA, Lowry PJ, Vale WW (1991) Cloning and characterization of the cDNAs for human and rat corticotropin releasing factor–BPs. Nature 349:423–425.

Reul JM, Holsboer F (2002) Corticotropin–releasing factor receptors 1 and 2 anxiety and depression. Curr. Opin Pharmacol 2:23–33.

Reyes TM, Lewis K, Perrin MH, Kunitake KS, Vaughan J, Arias CA, Hogenesch JB, Gulyas J, Rivier J, Vale WW, Sawchenko PE (2001) Urocortin II: A member of the corticotropin–releasing factor (CRF) neuropeptide family that is selectively bound by type 2 CRF receptors. Proc Natl Acad Sci U S A 98:2843–2848.

Tache Y, Martinez V, Million M, Wang L (2001) Stress and the gastrointestinal tract III. Stress–related alterations of gut motor function: role of brain corticotropin–releasing factor recptors. Am J Physiol Gastrointest Liver Physiol 280:G173–177.

Takahashi LK (2001) Role of CRF(1) and CRF(2) receptors in fear and anxiety. Neurosci Biobehav Rev 25:627–636.

Takahashi LK, Ho SP, Livanov V, Graciani N, Americ SP (2001) Antagonism of CRF(2) receptors produces anxiolytic behavior in animal models of anxiety. Brain Res 902:135–142.

Vanitallie TB (2002) Stress: A risk factor for serious illness. Metabolism 51:40–45.

Vaughan J, Donaldson C, Bittencourt J, Perrin MH, Lewis K, Sutton S, Chan R, Turnbull AV, Lovejoy D, Rivier C, et al. (1995) Urocortin, a mammalian neuropeptide related to fish urotensin I and to corticotropin–releasing factor. Nature 378:287–292.

Veith RC, Lewis N, Langohr JI, Murburg MM, Ashleigh EA, Castillo S, Peskind ER, Pascualy M, Bissette G, Nemeroff CB, Raskin MA (1993) Effect of desipramine on cerebrospinal fluid concentrations of corticotropin–releasing factor in human subjects. Psychiatry Res 46:1–8.

Zobel AW, Nickel T, Kunzel HE, Ackl N, Sonntag A, Ising M, Holsboer F (2000) Effects of the high–affinity corticotropin–releasing hormone receptor 1 antagonist R121919 in major depression: the first 20 patients treated. J Psychiatr Res 34:171–181.

Behan, Dominic C., et al. (1995) Displacement of corticotropin releasing factor from its binding protein as a possible treatment for Alzheimer's disease. Nature 378:284–287.

Behan, Dominic C., et al. (1992) Cloning and Structure of the Human Corticotropin Releasing Factor–Binding Protein Gene (CRHBP). Genomics 16:63–68.

Ruopin Chen, et al., Expression cloning of a human corticotropin–releasing–factor receptor, Proc. Natl. Acad. Sci. USA, Oct. 1993, vol. 90, pp. 8967–8971.

* cited by examiner

Fig. 1

(SEQ ID NO:1)

```
AGGCAGGTGGATCATTTGAGGTCAGAAGTTCGAAACCATCATGGCCAACAAGGTGACACC    -4858
CCGTCTCTACTAAAAATACAAAAATTAGCTGGGTGTGGTGGTGCACACCTGTAATCCCAG    -4798
CTACTGGGGAGGCTGAGGCAGGAGAATTGCTTGAATCTGGGAGGCAGAGGTTGCAGTGTC    -4738
CTGAGATTATGCCACAGCACTCCAGCCTGGGAAACAGAGTGAGACTCTGTCTCTAAATAA    -4678
ATAAATAAATAAATAAATGCCTTCTGCACAGCAAAGGAAATGATCAACAGGGTGCAAAGG    -4618
TAACCTACATAATGGGAGAAAATACTTACCAACCATGTATCTGATAAGTGGTTAATATCC    -4558
AAAATATATAAGAAACTCCTACAACTCAGCAAAAAACCTATTAAGTCATTTTAAAAATGG    -4498
GCTAAGGACTTGAATAGACATTTCTCCAAAGAAGACATACAAATGGCCAACCAGTATATG    -4438
AAAAGATGCTCAATATCACCAAGATCAAGAAAATGCAAATCAAATCCACGACGAGACATC    -4378
ACCTCGAAACTGTTCAGATGGCTATCATCAAAAAGATACAAGATGACAAGTGCTGGCAGG    -4318
GAAAAAGGAAACCCTGGCCACTGTTAGAGGGAATGGCAATTAGCACAGCCATTATGGAA    -4258
AACACTATGGACTTTCCTCAAAAAATTAAAATAGAGGAGTATTGTATGAAAGGAGAGAAG    -4198
GTTAACATTCCCCTTGACAAGAGGAACAGAAAATCAAATACCGTGTGTCCTCAGTTATAA    -4138
GTGGGAGCTAAATGATGAGAACAAACACATGGACACATAGAGGGAAATGACACATACTGG    -4078
GGCCTATTGGAAGTTGGAGGGTGGGAGGAGGGAGAGGATCAGGAAAAATAACTGATGGGT    -4018
ACTAGGCTTAATACCTGGGTGAAGAAATGATCTGTACAACAAACCTCCATGACACATGTT    -3958
TACCTATGTGACAAACCTGCACATGTACTCCTGAAGTTAAAATAAAAGTTTTTAGGCCAG    -3898
GCACAGTGGCTCACGCCTGTAATCCCAGCACTTTGGGAGGCCAACGTGGGCAGATCACGA    -3838
GGTCAGGAGATCAAGACCATCCTGGCTAACACGGTGAAACCCCGTCTCTACTAAACATAC    -3778
AAAAAAATTAGCCTGGTGTGGTGGCAGGCGCCTGTAGTACCAGCTACTCGGGAGGCTGAG    -3718
ACAGGAGAATGGCGTGGACCCAGGAGGCAGAGCTTGCAGTGAGCCAAGATCATGCCACTG    -3658
CACTCCAGCCTGGGCAACACAGCAAGACTCCATCTCAAAAAAAAATAATGAAAAAATAA    -3598
AAGTTTTATAAAAATAGAATGGTAATATGATTCAGCAAGCCCACTTCTGCGTATTTTTC    -3538
CAAAAGAATTGAAATCAGTATGTTGAAGACATACCTGCATTCCTATGTTCGTTGCACCAG    -3478
TATTCACAATAGCTAAGATGTGGAAACAACCTAAATGTTGACGAATGAATAAAGAAAATG    -3418
TGGTATATACATACAATGGAATATTACTCAGTCTGAGAAAAGAGGAAATCCTTGTCATAT    -3358
ACTACAGCATGGATGAAACTTGAGGACATTATGCTAAGTGAAAGATGCCAGCCACAAAAG    -3298
```

```
GGCAAATACTGTACGATTACACTTACATGAGCTATCTAAAATAGTGAGACTCGTAGAAGA    -3238

AGACAGTAGAATGATGGTTGCAGGGATTGGGAGGAGGGTAAAATGGGGAATCGCTAATAA    -3178

TGGGTATAAAGTTTCAGCTATGCAAGATGAATAAGTTCCAGAGATCTGTTGTACAACGTT    -3118

GTGCCTATAGTTGATAATATTGTGTTGTGCACTTAAATATCTTTTAAGAGAGTAGATCTC    -3058

GTGTTTTAACTCTTCTTACCACAATAAAATAAAAATAATAGCTACATTCATTCAAACAAA    -2998

TCATCTTGAAAGCAATGGAAAACTATTTGGTGGTTGTTGTTGTTGGCTAACTACAATGAG    -2938

TTTTATTCAGTAGTCTTTATTTCTTAAAGAACGCAATGATATGTTCTATTTTCTAACATT    -2878

TCAACTAATCGATTAATCAGGAAAGGAAAAAGGAAGTTCATCTAAAGCATGGATTAGTGA    -2818

TGTTCTAAGTTGACGTGATAAATAAAAGAAAAAATTTATTATCACAGGTCATATTACAAC    -2758

TTCTAACTTGCGTGCATAGGGATTTTGTGGTCACCCTGAAAACATGGCCTATAATGTGAC    -2698

TGTGAAAGCCAAGTGCAGCCTGTGGAGGCTCTGCCATGAAGTGTCAGAAGTTCTCTGTGT    -2638

GTGTCTCATCAGTCTAGGCACAATTTTAAATTCTGCACCTGCCCCCATGTCCATGGATTG    -2578

AATATGGATCTGCTATTGTGTGGCCACCCTGGCCTTCAGGCTTAACATAGGTGACAATTT    -2518

GCTCTGGGGCTTTGTGAAGAAAAAATGTCTTATTCCTACCTAACAAAAAGAAAGTATTA    -2458

ACCCTGCCTAACAATAGTCGAAGACCCAAAAAACACCTATCCGGGACTGTATAACATCAA    -2398

CACTGGAGAAGCTATCTGGAAAAATATGGAGAAAAACTGAAATATTTGAAAGTAATGGAG    -2338

GTTAACATACAGGTAATTTCCAATCAGCATACTTGGGGACTCTGAGTTTTCCCAGAACAT    -2278

ATTTAAAAAAAAAATCCAGTTTGCTTGAACAAACAACTTTCAAATATTAAGCTAATTGTT    -2218

TGAATGACCAAAGCAGTCCATGAAAATAATTTATCCTTAGTCTTCACACATAGGCCTACT    -2158

TATTGCCCAGAAAATTTTTCTTCGGCCTAATCCAAATTACTCTTCCATTTCTCTCACCTA    -2098

TTTTTAATACTTTCTCTCAGAGAGAATGGCTACCTGGCTTCTCCTTGTCTTCCAATTTAA    -2038

TCTTCTTAGTTTTTCTCGATAGCTTGTAGTTTCCATCTTTTAATTACCATTAATTTTTTT    -1978

TTTTTTAGAAAAGGTAGTTTCCACTGGCTTAGTAGATATTTACCAAACTGGTGAAAACTA    -1918

CACATTAATTTATCCACCTAGAATTTGGTGGGAATGAGGTCCATCTTGTACTATAATTTG    -1858

TGGATTAAGTAAAATCAGATGCTATGCTATGATGTTTGTAAAATCAGTCACTATGTTAGT    -1798

GCTCATTCATCCCAGCTCTTGCTGTGTGTGGTTCCTGAGGAGTGGGCATCATGACAGCAG    -1738

GGTGGGAACATCACTGTTGTCTGTGCACGTGCATGCGTGCATGTGTGTGCACATGTGC    -1678

ACATGTGCATATGCTTGTAAAGGGGCTGGCTGGAGAAGAATGTCTCCTTGGTGATGCTAA    -1618

CAAAGCAACATTGAGCTGGAGTGACATCAGGTGCCAGACCCCCTAAGAGGTAAAGGCAGA    -1558
```

```
GGTCTCCAAGGTGGGTGCTGGACTGAATTCTGGGAACAGGCCAAGGGCTGTGGCTACATC  -1498
AATGGGAAAGAGAAGAGGGCCTGTGGCATGCCTGGTGAGTGGGCCTAAGGCTCCCTCTAG  -1438
GCACAAAAGGGTGGGAGATAGAGCTGAAGATGGCCTGGCATGTTTGAGGCCAGCAAGTT   -1378
GGGGTTAAGTTGTTTGTTTTTCTCCTCTTTTATTCCTCCCAGGTTTCTTTATAACCTTTT  -1318
CAAAATTCAGGCATCTAAACAGCCCTTGGGATGAGAAGGACATGGTGGCCAGTGTCCATG  -1258
AGCTTTAGGTACTCTTTTCCCTCTCACTGTCTGTGGTCTGAGGACTGCTTACAAAGTTGG  -1198
ACTGTGGCACGAAGGCCTCCTGATTAAACCAACAAAGAGGCCGCCTCTCCAGAGCTCAGA  -1138
ATTGTCCTGACATGAAAATAATCAAGTTCTGACACTGCCAGGATAATTACTGTTTAATTT  -1078
CGAGTATTTAAAACTGAAAATATAGCCATTCCTTCCTTTATAACTCTGTATTATGGTCT   -1018
ATTTGTAATAATTGTAATAACAATGCTTGGTGCAGAGACTGGAAAGGGGTAGGAAAGCCA  -958
ATAGTGGAGCATCCTCATGTTTCCCACAGTTTTGGACACAAAGAAGAAATTCTCTTCTCT  -898
CCTGATAAGCAGAGATAAGCTTATACTTATTTCCGGATCCCTAAGTCATCTTTTTAGCCC  -838
TGCAAATTTGCTGGTGAGCAGTTACAATAAAGCTTCCTGGCAGTTCCTTCTACCAGAGTG  -778
TTAAAGTAATCCAGGTATTTGAAGGCACGAAATGGAATGACTTAATCTCATCTCTCAGTG  -718
GTTCAGATGGATGCGAAGGTCATGGCTACAGCTACCTGGTCTAGGAGTGTGTACATCATG  -658
TAAACATCCAGGTCAAGTGACAGAGCTCAGCTAAAATCCAGAAGTCCCCTGACACCAGAG  -598
TTAGTTTTCCATGAAAGAAATGCCTATAAGAAACTGGACCAGGATAAAGCAAAGAGTAAG  -538
GGGCAGGAAGAAAGCTTATAATTGCATTACTGCAATCTTCTGCAAAATCAGACTTCTGCT  -478
TCTGTTCCACCTCTTTAAAGCTGAAAATGCCTCAAGTTTCTTACTGAGAGACATGAGAAA  -418
TTCCATGAATACTAAATTCTTTGACAATTTCTAGCATGGTTTCATCCAAGGTTATGTGAT  -358
GAGGCTGCATAATATAGGCTCTATATGTTTGGGTATTTTATGCGTGTATGTAACTTTGTC  -298
ACTTTGATTTGCAAAATGGAAAATTCCCTGAATGCCCACAGAAAAGTATAATGTAGCATT  -238
TAGCAGGTCAACAAAATGCACTCCCTTATTCTTTGTCTCCGCCTCATTCTCCAACACTTT  -178
AGTGCACTAAGTTGTAGTGACTGAAATCATTCTTGGTGAATAATGCTGGGCCACGCTGAA  -118
AATTTGTGGCTGAGAGCTGGACCCTCGTCATCGCCACGTACTCTGTCAATGAGACAGGGT   -58
AACCCATGGTTACTGAGCTCCGATCAGTTAAGGGGCAGAGAGCCTCCGCTCCCCACTGCT   +3
CTATAAAAGAGACCCAGCAAAGGGACCCTACCAGCTTCTAGCTCTCAGTCTGCGCGAGGG  +63
TGTAGGAAGGAAAGCCCAGGA+84
```

PROMOTER SEQUENCES FOR CORTICOTROPIN RELEASING-FACTOR BINDING PROTEIN AND USE THEREOF

CROSS-REFERENCE TO RELATED APPLICATION

This application claims the benefit of U.S. provisional application Ser. No. 60/415,586, filed on Oct. 2, 2002.

STATEMENT REGARDING FEDERALLY SPONSORED RESEARCH OR DEVELOPMENT

This invention was made with United States government support awarded by the following agency: NIH MH40855. The United States has certain rights in this invention.

BACKGROUND OF THE INVENTION

In modern society stress and its consequences are prevalent and result in considerable distress and alterations in physical health and social and occupational functioning. At its extreme, stress can lead to disabling neuropsychiatric problems which include depression, anxiety disorders, post-traumatic stress disorder and other illnesses (Mitchell, 1998; Arborelius et al., 1999). Recent studies demonstrate the potent effects of stress on the body and brain. For example, chronic and intense stress can result in alterations in the region of the brain that plays an important role in memory (McGaugh and Roozendaal, 2002). In addition, stress can negatively impact cardiovascular function, immune function and gastrointestinal physiology (Tache et al., 2001; Beglinger and Degen, 2002; Coste et al., 2002; Gasparotto et al., 2002; Vanitallie, 2002).

It is estimated that 10% of the population suffers from depression and another 15% from clinically significant anxiety. This high incidence of stress-related problems is reflected by the fact that approximately 50% of visits to primary care doctors are stress and/or psychologically related.

Current treatments for stress and its disorders are highly sought after and include the traditional anti-anxiety drugs like Valium and Xanax. More recently newer antidepressants like Prozac have been used to treat depression, anxiety and other stress related problems. It is estimated that $13 billion was spent last year in the U.S. on drugs like Prozac and Paxil. However, these treatments still suffer from lack of efficacy in approximately 30% of the individuals treated. Among those who do respond, only about 50% of them will return to normal function. In addition, these treatments have bothersome side-effects (50% have marked sexual dysfunction) which make treatment with these drugs unacceptable for many individuals. Since depression and anxiety are recurrent and chronic disorders it is important that patients are comfortable taking their medication over a long period of time. Overactivity of the corticotropin-releasing factor (CRF) system is implicated in depression and anxiety and treatments aimed at this system may be very effective (Reul and Holsboer, 2002).

Studies in animals demonstrate that antagonism of the CRF system blocks the distress and physical effects related to stress (Takahashi et al., 2001; Bakshi et al., 2002). Studies in humans show that the CRF system in the brain is overactive in patients with depression, anxiety disorders and other neuropsychiatric problems (Nemeroff, 1989; Chappell et al., 1996; Fossey et al., 1996; Bremner et al., 1997; Mitchell, 1998; Baker et al., 1999). In addition, human and animal studies demonstrate that many effective antidepressant treatments decrease brain CRF activity (Veith et al., 1993). Based on these findings the pharmaceutical industry is currently intensively searching for orally administered compounds that will block or reduce the effects of CRF in the brain. Already some compounds have been identified and are in the early stages of human studies (Zobel et al., 2000).

The CRF system is now known to consist of at least seven components. CRF is a neurotransmitter that is released from neurons and has its effects by interacting with CRF receptors located on adjacent brain cells. Urocortin (UCN), urocortin II (UCN II) and urocortin III (UCN III) are other neurotransmitters similar to CRF that also interact with the system (Vaughan et al., 1995; Lewis et al., 2001; Reyes et al., 2001). Once stimulated the receptors activate intracellular processes which mediate the stress effects.

CRF produces its effects by interacting with two different receptors termed CRF1 and CRF2 (Chen et al., 1993; Perrin et al., 1995). Multiple isoforms of the two receptors exist. For example, there are three different isoforms of the CRF2 receptor, termed "CRF2α," "CRF2β" and "CRF2γ" (Lovenberg et al., 1995; Kostich et al., 1998). In addition to CRF1 and CRF2 receptors, there also exists a protein, termed "CRF binding protein" (CRF-BP), that is found in brain cells and functions to inactivate CRF after it is released (Potter et al., 1991).

The CRF-BP is a 37 kDa protein that binds CRF and urocortin peptides with an affinity similar to the CRF receptors (Behan, et al., 1995). CRF-BP is thought to limit the effects of CRF on CRF receptors. For example, CRF-BP blunts the effects of CRF on ACTH release from the pituitary and placental cells in vitro (Linton, et al., 1990). In addition, approximately 60–95% of CRF is complexed by CRF-BP in most regions of the normal human brain (Behan, et al., 1997). In order to regulate the expression of CRF-BP, through which the activity of CRF and urocortin peptides can be regulated, it is important to understand how the CRF-BP promoter region works. However, no sequence information on CRF-BP promoter is currently available.

SUMMARY OF THE INVENTION

The present invention relates to the determination of the nucleotide sequence of the human CRF-BP promoter and various fragments thereof. In one aspect, the present invention relates to an isolated nucleic acid containing a human CRF-BP promoter sequence selected from the 4917 bp upstream of the transcription start point (TSP) (nucleotides 1 to 4917 of SEQ ID NO:1), a functional fragment thereof, or a complement of any of the foregoing. Examples of fragments that can drive transcription over background level include but are not limited to the 4402 bp upstream of the TSP (nucleotides 516 to 4917 of SEQ ID NO:1), the 3317 bp upstream of the TSP (nucleotides 1601 to 4917 of SEQ ID NO:1), the 2971 bp upstream of the TSP (nucleotides 1947 to 4917 of SEQ ID NO:1), the 2415 bp upstream of the TSP (nucleotides 2503 to 4917 of SEQ ID NO:1), the 1889 bp upstream of the TSP (nucleotides 3029 to 4917 of SEQ ID NO:1), the 1386 bp upstream of the TSP (nucleotides 3532 to 4917 of SEQ ID NO:1), the 955 bp upstream of the TSP (nucleotides 3963 to 4917 of SEQ ID NO:1), the 381 bp upstream of the TSP (nucleotides 4537 to 4917 of SEQ ID NO:1), the 271 bp upstream of the TSP (nucleotides 4647 to 4917 of SEQ ID NO:1), the 208 bp upstream of the TSP (nucleotides 4710 to 4917 of SEQ ID NO:1), and the 91 bp upstream of the TSP (nucleotides 4827 to 4917 of SEQ ID NO:1). Other functional fragments can be readily determined by a skilled artisan. The term "human CRF-BP promoter sequence" is used broadly to encompass any of the sequences or fragments described above.

In another aspect, the present invention relates to a nucleic acid that contains a human CRF-BP promoter sequence and a heterologous reporter gene operably linked to the sequence. The nucleic acid can be an expression vector and can be provided in a host cell.

Other aspects of the invention relate to methods of screening for agents that may alter the activity of human CRF-BP promoter, methods of determining whether a fragment of the human CRF-BP promoter can drive transcription under specific conditions, methods of determining which region of the human CRF-BP promoter interacts with an agent that is known to alter the activity of the promoter, and methods of screening for agents that can affect the modulation of the human CRF-BP promoter activity by cAMP level.

An agent identified by the method of the present invention may be used to treat various psychopathologies, including but not limited to depression, generalized anxiety, social anxiety, post traumatic stress and panic disorder. Additionally, an agent identified may also be useful in the treatment of other illnesses associated with stress such as irritable bowel syndrome and heart disease.

Besides controlling how much CRF-BP is expressed, the promoter region of the human CRF-BP gene is also responsible for determining where in the body and when during development CRF-BP is expressed. Thus, fragments of the human CRF-BP promoter region disclosed herein can be used to identify those elements that are important for tissue and development stage specific expression by conducting experiments in cells from specific tissues and development stages. Once these elements are identified, agents that can alter tissue and development stage specific expression can be identified. These agents may be advantageous in treating stress-related problems over prior art treatment strategies because the agents target CRF-BP expression in specific regions that are most important in an illness. Thus side effects seen in prior art receptor antagonists treatment due to indiscriminate inhibition of the receptor activity throughout the brain and body can be avoided. For example, the locus coeruleus is located deep in the brain and is thought to be pivotal in mediating the effects of CRF and related peptides in depression and anxiety. Drugs that specifically target CRF-BP in the locus coeruleus will leave other sites (cortex, brain stem, heart, and hypothalamus) unaffected.

BRIEF DESCRIPTION OF THE SEVERAL VIEWS OF THE DRAWINGS

FIG. 1 shows the CRF-BP promoter region. The arrow identifies the putative TSP which corresponds to position +1. The numbering in the right hand margin is relative to this putative TSP.

DETAILED DESCRIPTION OF THE INVENTION

The term "isolated nucleic acid" used herein means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of clones, e.g., as these occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

We have cloned the promoter region of the human CRF-BP gene. Various fragments of the promoter region have been generated and tested for promoter activity in cultured cells. Sequences and activities of various sequences are shown in the Example below. Further, we have shown that the activity of the human CRF-BP promoter can be regulated by cAMP.

In one aspect, the present invention relates to an isolated nucleic acid containing a human CRF-BP promoter sequence selected from the 4917 bp upstream of the TSP (nucleotides 1 to 4917 of SEQ ID NO:1), a functional fragment thereof, or a complement of any of the forgoing. By "a functional fragment," we mean that the fragment contains at least one activator or repressor for gene expression under specific conditions. An activator functions to drive gene expression to above a background level and a repressor functions to bring the expression back toward the background level. If both activators and repressors are present, the actual expression level will be determined by the combined effects of the activators and repressors. The background level is defined as the expression level in the absence of any promoter sequence or in the presence of an unrelated nucleotide sequence. It should be noted that all functional fragments described above are useful in the screening method and other methods provided below. It is not required that the functional fragment drives the expression to above a background level. It is only necessary that perturbation of the fragment's function can be measured. Fragments that can increase downstream gene expression to above the background level include but are not limited to the 4402 bp upstream of the TSP (nucleotides 516 to 4917 of SEQ ID NO:1), the 3317 bp upstream of the TSP (nucleotides 1601 to 4917 of SEQ ID NO:1), the 2971 bp upstream of the TSP (nucleotides 1947 to 4917 of SEQ ID NO:1), the 2415 bp upstream of the TSP (nucleotides 2503 to 4917 of SEQ ID NO:1), the 1889 bp upstream of the TSP (nucleotides 3029 to 4917 of SEQ ID NO:1), the 1386 bp upstream of the TSP (nucleotides 3532 to 4917 of SEQ ID NO:1), the 955 bp upstream of the TSP (nucleotides 3963 to 4917 of SEQ ID NO:1), the 381 bp upstream of the TSP (nucleotides 4537 to 4917 of SEQ ID NO:1), the 271 bp upstream of the TSP (nucleotides 4647 to 4917 of SEQ ID NO:1), the 208 bp upstream of the TSP (nucleotides 4710 to 4917 of SEQ ID NO:1), and the 91 bp upstream of the TSP (nucleotides 4827 to 4917 of SEQ ID NO:1). Other functional fragments can be readily determined by a skilled artisan using known techniques such as that described in the Example below.

The term "human CRF-BP promoter sequence" is used broadly to encompass any of the sequences or fragments described above. Preferably, a human CRF-BP promoter sequence contains at least 50 bp upstream from the TSP (nucleotides 4868 to 4917 of SEQ ID NO:1). A human CRF-BP promoter sequence may be attached to contiguous regions of the sequence in SEQ ID NO:1 or may be attached to other sequences as long as the other sequences do not abolish the function of the promoter sequence. We specifically envision that one may wish to test fragments in which naturally-occurring sections of the sequence of SEQ ID NO:1 have been replaced by "spacer DNA," or non-naturally occurring sequences. We also specifically envision that one may wish to test versions of the sequence of SEQ ID NO:1 in which sections have been deleted. These constructs, as long as they comprise the first 50 nucleotides of the promoter, are "promoter sequences" of the present invention.

One of skill in the art could make innocuous substitutions in a sequence of the present invention and create a functionally identical promoter. We envision that such substitutions would not comprise more that 5% of the total sequence and would not result in a substantial change of promoter activity, as measured below.

In another aspect, the present invention relates to a nucleic acid, which can but does not have to be an expression vector, that contains a human CRF-BP promoter sequence as described above and a heterologous reporter gene operably linked to the sequence. Such a nucleic acid is useful in many of the methods described below, which involve the determination of the promoter activity of a promoter sequence. The term "reporter gene" is defined here to encompass any polynucleotide the transcription of which under the control of a promoter sequence, the subsequent translation thereof, or both can be readily detected by a skilled artisan. Thus, the reporter gene does not have to encode a full length protein. In some instances, the reporter gene can even be an oligonucleotide. In one embodiment, the reporter gene is a polynucleotide that encodes a protein with a detectable activity.

In another aspect, the present invention relates to a cultured cell that contains a nucleic acid described above. In one embodiment, the cell is a primary cultured cell such as a primary cultured central nervous system cell. In another embodiment, the cell is a cell of an immortalized cell line.

In another aspect, the present invention relates to a method for screening for an agent that can alter the human CRF-BP promoter activity, which is envisioned to have significant therapeutic potential in the treatment of various psychopathologies. The method first involves providing a nucleic acid that contains a human CRF-BP promoter sequence described above that is operably linked to a reporter gene. The nucleic acid is next exposed to conditions suitable for the promoter sequence to drive the transcription of the reporter gene. Two groups of nucleic acids can be set up here. In one group, the expression of the reporter gene is measured in the presence of a test agent. In the other group (control group), the expression is measured in the absence of the test agent. The expression of the reporter gene in both groups can then be compared. A higher or lower expression in the test agent group than in the control group indicates that the agent may alter human CRF-BP promoter activity.

A skilled artisan is familiar with the assay systems that can be used for measuring the expression of a reporter under the control of a promoter sequence and the present invention is not limited to any particular assay systems. In the Example described below, an expression vector containing a human CRF-BP promoter sequence and a luciferase reporter gene was introduced into CHO-K1 cells and the expression of the reporter gene was measured by the luciferase activity. It is understood that other cells and reporter genes can also be used. Furthermore, the expression of the reporter gene can also be measured at the mRNA level or at the protein level with a method other than assaying the enzyme activity. For example, the amount of a reporter gene product can be measured by the use of an antibody specific for the product using an ELISA assay.

As another example, a cell-free transcription assay or transcription-translation assay can be used to measure the expression of a reporter gene. When a transcription assay is used, the expression of the reporter gene can be determined at the mRNA level. When a transcription-translation assay is used, the expression of the reporter gene can be measured at the mRNA level, the protein or peptide level, or both.

The suitable conditions for different human CRF-BP promoter sequences to drive transcription may be different. For example, a particular human CRF-BP promoter sequence may drive transcription more effectively in one cell type than in another. For a particular human CRF-BP promoter sequence, suitable transcription conditions, if not already known, can be readily determined by a skilled artisan.

In another aspect, the present invention relates to a method for determining whether a fragment of the 4917 bp upstream of the TSP of the human CRF-BP promoter region is functional under a set of conditions of interest (e.g., in a specific cell type). The method involves providing a nucleic acid that contains the fragment and a heterologous reporter gene operably linked to the fragment, subjecting the nucleic acid to the set of conditions of interest, measuring the expression level of the reporter gene, and comparing the expression level to a suitable control wherein a higher or lower than control expression level indicates that the fragment is functional. Suitable controls can be readily determined by a skilled artisan. An isolated nucleic acid that contains a functional fragment identified, a nucleic acid that contains the functional fragment operably linked to a heterologous reporter gene, and a host cell that contains the nucleic acid with the functional fragment and the reporter gene are also within the scope of the present invention. Also within the scope of the present invention is a method of using the functional fragment identified to screen for agents that may alter the activity of human CRF-BP promoter as described above.

In another aspect, the present invention relates to a method of determining which region of the human CRF-BP promoter interacts with an agent known to alter the activity of the promoter. The method first involves providing multiple groups of nucleic acids in which a reporter gene is operably linked to a fragment of the 4917 bp upstream of the TSP of the human CRF-BP promoter and wherein the nucleic acids of the same group contain the same fragment and the nucleic acids in different groups contain different fragments. The nucleic acids are next subjected to conditions suitable for the fragments to drive the transcription of the reporter gene. The expression of the reporter gene in the absence and presence of the agent is then measured and compared, and the effects of the agent on the promoter activity of different fragments are determined. Finally, the effects of the agent on the promoter activity of different fragments are compared and the region of the human CRF-BP promoter that interacts with the agent can be identified.

In another aspect, the present invention relates to a method for screening for an agent that can affect the modulation of human CRF-BP promoter activity by cellular cAMP level. The method involves providing a host cell that contains a human CRF-BP promoter sequence and a reporter gene operably linked to the promoter sequence wherein the expression of the reporter gene controlled by the promoter sequence can be modulated by cellular cAMP level, changing the cellular cAMP level, exposing the cell to a test agent, determining the expression level of the reporter gene, and comparing the expression level to that of a control cell that is not exposed to the test agent wherein a higher or lower than control expression indicates that the test agent can affect the modulation of the human CRF-BP promoter activity by cAMP level.

In the Example below, three CRF-BP promoter sequences were tested and the activities of all three were shown to be regulated by cellular cAMP level. It is expected that the promoter activities of all fragments described in the Example below can be regulated by cAMP and thus suitable for the method. Other such fragments can be readily identified by a skilled artisan using known techniques such as that used in the Example. Methods and agents that can be used to change the cellular cAMP level are known to a skilled artisan. In the Example below, forskolin and IBMX were used to increase the cAMP level. Other methods of changing the cellular cAMP level can also be used.

EXAMPLE

Human CRF-BP Promoter

The human CRF-BP promoter was obtained by screening a human placental genomic library constructed in Lambda FIX® II obtained from Stratagene (La Jolla, Calif.). The library was probed with a $^{32}$P-labelled fragment of the human CRF-BP cDNA (Sambrook, et al., 1989), which corresponded to bases 561 to 1110 of the cDNA (GenBank accession # XM_003672; Potter, et al., 1991). Five positive clones were plaque-purified and directly sequenced using a primer located in exon 1 near the boundary with the promoter region. This sequencing revealed that at least three of the clones contained promoter sequence. One of these clones was used as template for PCR. A 5.5 kb fragment corresponding to the promoter region was amplified by PCR from this genomic clone. The fragment was then subcloned into pCR2.1 TOPO using the T/A cloning kit (InVitrogen, Carlsbad, Calif.). The 5.5 kb insert was next cut out of pCR2.1 TOPO with Spe I and Xho I and subcloned into pGL3-basic that had been digested with Nhe I and Xho I.

To generate a series of fragments of the promoter, we used a common reverse (3') primer that ended 84 bp downstream of the putative transcription start point (TSP), we generated sequentially smaller fragments of the CRF-BP promoter region through PCR with several forward (5') primers. The constructs generated were from −4917, −4402, −3317, −2971, −2415, −1889, −1386, −955, −381, −271, −208, and −91 bp relative to the TSP through +84 bp (referred to as the −4917, −4402, −3317, −2971, −2415, −1889, −1386, −955, −381, −271, −208, and −91 bp constructs, respectively). These PCR products were subcloned using T/A cloning into the vector pCR2.1 TOPO (Invitrogen Life Technologies, Carlsbad, Calif.). The inserts were then removed by digestion with Spe I and EcoR V and subcloned into pGL3-basic that had been digested with Nhe I and Sma I.

The numbering above is based on our identification of the TSP through the use of 5' rapid amplification of cDNA ends (RACE) reactions. We utilized the SMART RACE cDNA amplification kit (Clontech, Palo Alto, Calif.) for this purpose. MMLV reverse transcriptase, upon reaching the end of an RNA template, exhibits terminal transferase activity, adding 3–5 dC's at the 3' end of the first-strand cDNA. The Clontech RACE kit utilizes this additional sequence to attach a common oligo (SMART A oligo) to the 5' end of an mRNA during the second-strand cDNA synthesis reaction. Using the cDNA from this reaction, the SMART A oligo, and a reverse primer specific to known sequence of CRF-BP mRNA (CACCCTCGCGCAGACTGAGAGC (SEQ ID NO:2); position +65 at 5' end), a PCR reaction was performed. The product of this reaction should yield the full 5' length of the CRF-BP mRNA.

By sequencing this product, we were able to define the 5' end of the CRF-BP mRNA. This is denoted as the TSP in FIG. 1 (SEQ ID NO:1) and is designated as position +1. The CRF-BP promoter sequence comprises the genomic DNA sequence upstream of this TSP. All constructs used in the transfection experiments are numbered relative to the TSP.

Production of Transfected Cell Lines

The above constructs containing the human CRF-BP promoter fragments placed upstream of the firefly luciferase gene can be used to transfect immortalized cell lines. The constructs were transfected into CHO-K1 cells using Lipofectamine 2000 (Invitrogen Life Technologies). Primary cultures of the central nervous system, as well as additional immortalized cell lines, are also appropriate for these transfections. To control for transfection efficiency, the cells can be co-transfected with the pRL-TK vector (Promega, Madison, Wis.). The pRL-TK vector contains the *Renilla* luciferase gene downstream of the herpes simplex virus thymidine kinase promoter, a promoter which provides low to moderate levels of expression. Cell lysates can be assayed for total protein using the BCA assay (Pierce, Rockford, Ill.) to standardize for the protein extraction. The level of reporter gene expression from a standardized amount of cell extract can be quantified by measuring luciferase activity using a luminometer (Berthold Life Science, Bundoora, AU) and the dual-luciferase reporter assay system (Promega, Madison, Wis.). Firefly luciferase activity reflects CRF-BP promoter activity and *Renilla* luciferase activity can be used to normalize data can be used to normalize data between expirements.

Characterization of Basal Expression from CRF-BP Promoter Fragments

Figure 2:
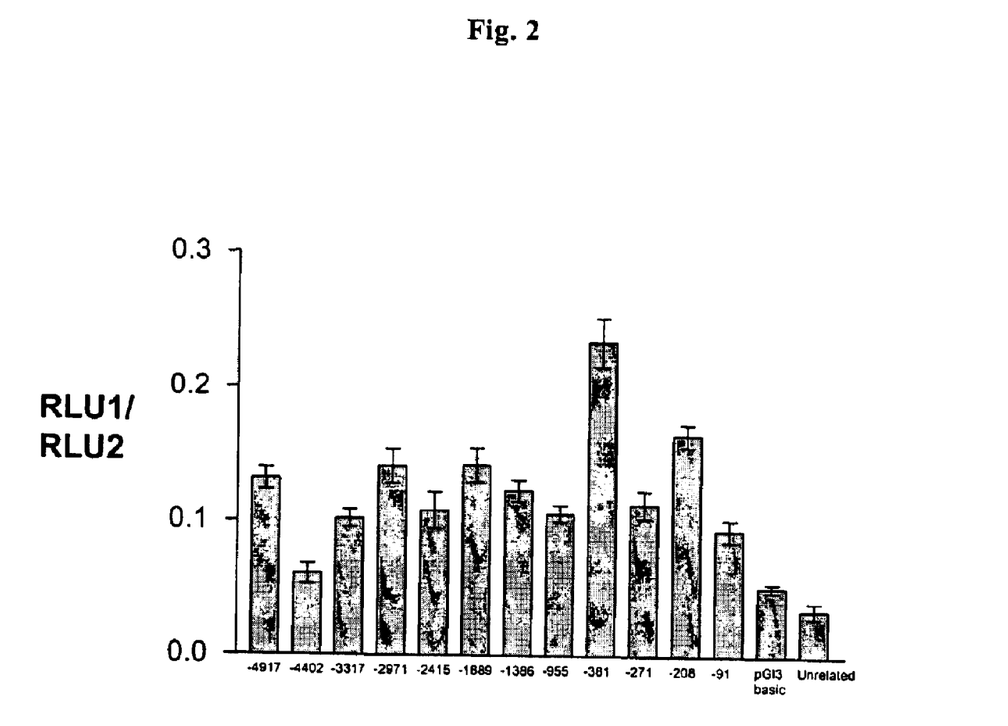
FIG. 2 shows basal levels of expression from CRF-BP promoter fragments in CHO-K1 culture.

Using the methods described above, transient transfections of CHO-K1 cultures were assayed for reporter gene expression (See FIG. 2). In these experiments, two basic controls were utilized. The cultures referred to as "pGL3 basic" were transfected with a pGL3 firefly luciferase reporter construct that did not contain an experimental promoter, and with the pRL-TK *renilla* luciferase vector. These cultures should demonstrate a very low level of expression (background levels) and may be considered negative controls. The cultures referred to as "unrelated" were transfected with a construct containing 1916 bp of DNA sequence upstream of the firefly reporter gene and with the pRL-TK renilla luciferase vector. The 1916 bp of this construct were a random DNA sequence (Unrelated). These cultures were intended to demonstrate the specificity of our promoter constructs.

Analysis of the data by one-way ANOVA indicated a highly significant finding ($P<0.0001$; $F=2968$, $R^2=0.9969$). When P value was set less than 0.01, post-hoc analysis (Newman-Keuls multiple comparison test) indicated that the −4917, −2971, −1889, −1386, −381 and −208 promoter fragments exhibit significantly increased expression compared with the pGL3-basic vector. Levels of expression were generally very low, and these results suggested strong negative regulatory control on the CRF-BP promoter. Nonetheless, our highest levels of expression were 356% greater than the promoterless levels of expression (pGL3-basic), and our lowest levels of expression were 17% greater than promoterless levels. In addition, the unrelated DNA sequence was unable to drive expression (33% lower expression than pGL3-basic). Therefore, the CRF-BP promoter fragments functioned and they are appropriate tools to monitor CRF-BP specific transcription.

Figure 3:
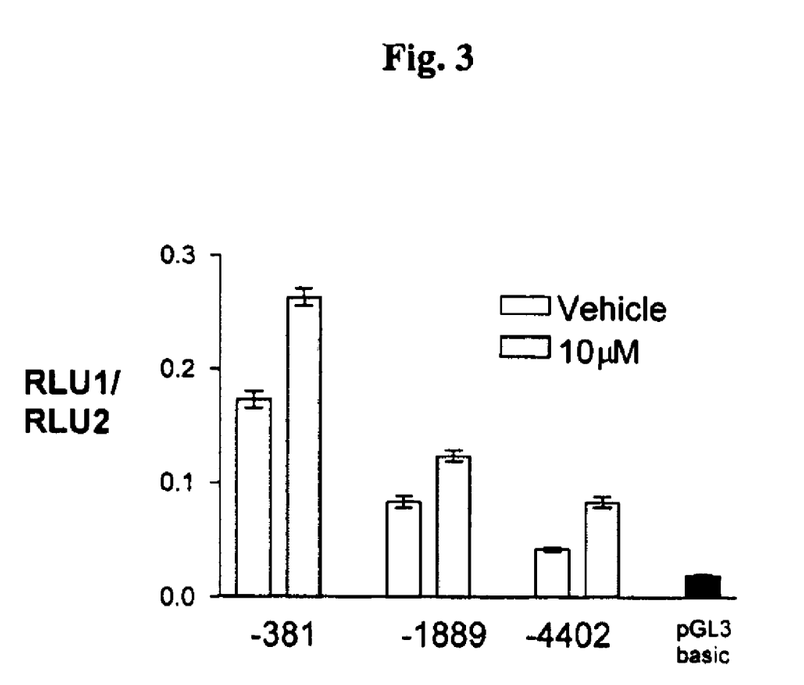
FIG. 3 shows forskolin-induced expression from CRF-BP promoter fragments in CHO-K1 culture.

Current understanding of the CRF-BP gene indicates that elevating intracellular cAMP levels should increase expression of the CRF-BP gene (Cortright, et al., 1997). Therefore, we treated transfected cultures with 10 µM forskolin, a compound known to increase intracellular cAMP, and measured expression from the CRF-BP promoter fragments (See FIG. 3). Isobutylmethylxanthine (IBMX) was included during the treatment at 0.25 mM to prevent cAMP degradation. Analysis of the data by one-way ANOVA indicated a highly significant finding ($P<0.0001$; $F=263.1$, $R^2=0.9741$). Post-hoc analysis (Newman-Keuls multiple comparison test) indicated that all examined promoter fragments had significantly increased expression compared with the pGL3 basic vector (−1889 and −381 $P<0.001$; −4402 $P<0.05$). Furthermore, expression from cultures treated with forskolin was significantly greater than expression from cultures transfected with the identical promoter fragment that received the vehicle ($P<0.001$ for all cases). These findings provided further evidence that the CRF-BP promoter fragments would be appropriate tools to monitor inducible CRF-BP specific transcription.

Although the invention has been described in connection with specific embodiments, it is understood that the invention is not limited to such specific embodiments but encompasses all such modifications and variations apparent to a skilled artisan that fall within the scope of the appended claims.

REFERENCES

Arborelius L, Owens M J, Plotsky P M, Nemeroff C B (1999) The role of corticotropin-releasing factor in depression and anxiety disorders. J Endocrinol 160:1–12.

Baker D G, West S A, Nicholson W E, Ekhator N N, Kasckow J W, Hill K K, Bruce A B, Orth D N, Geracioti T D, Jr. (1999) Serial CSF corticotropin-releasing hormone levels and adrenocortical activity in combat veterans with posttraumatic stress disorder. Am J Psychiatry 156:585–588.

Bakshi V P, Smith-Roe S, Newman S M, Grigoriadis D E, Kalin N H (2002) Reduction of stress-induced behavior by antagonism of corticotropin-releasing hormone 2 (CRF2) receptors in lateral septum or CRF1 receptors in amygdala. J Neurosci 22:2926–2935.

Beglinger C, Degen L (2002) Role of thyrotrophin releasing hormone and corticotrophin releasing factor in stress related alterations of gastrointestinal motor function. Gut 51 Suppl 1:145–149.

Behan D P, De Souza E B, Lowry P J, Potter E, Sawchenko P, Vale W W (1995) Corticotropin releasing factor (CRF) BP: a novel regulator of CRF and related peptides. Front Neuroendocrinol 16:362–382.

Behan D P, Khongsaly O, Owens J J, Chung H D, Nemeroff C B, DeSouza E G (1997) Corticotropin-Releasing Factor (CRF), CRF-BP (CRF-BP), and CRF/CRF-BP Complex in Alzheimer's Disease and Control Postmortem Human Brain. Journal of Neurochemistry 68:2053–2060.

Bremner J D, Licinio J, Darnell A, Krystal J H, Owens M J, Southwick S M, Nemeroff C B, Charney D S (1997) Elevated CSF corticotropin-releasing factor concentrations in posttraumatic stress disorder. Am J Psychiatry 154:624–629.

Chappell P, Leckman J, Goodman W, Bissette G, Pauls D, Anderson G, Riddle M, Scahill L, McDougle C, Cohen D (1996) Elevated cerebrospinal fluid corticotropin-releasing factor in Tourette's syndrome: comparison to obsessive compulsive disorder and normal controls. Biol Psychiatry 39:776–783.

Chen R, Lewis K A, Perrin M H, Vale W W (1993) Expression cloning of a human corticotropin-releasing-factor receptor. Proc Natl Acad Sci USA 90:8967–8971.

Cortright D, Goosens K, Lesh J, Seasholtz A (1997) Isolation and characterization of the rat corticotropin-releasing hormone (CRF) BP gene: Transcriptional regulation by cyclic adenosine monophosphate and CRF. Endocrinology 138:2098–2108.

Coste S C, Quintos R F, Stenzel-Poore M P (2002) Corticotropin-releasing hormone-related peptides and receptors. Emergent regulators of cardiovascular adaptations to stress. Trends Cardiovasc Med 12:176–182.

Fossey M D, Lydiard R B, Ballenger J C, Laraia M T, Bissette G, Nemeroff C B (1996) Cerebrospinal fluid corticotropin-releasing factor concentrations in patients with anxiety disorders and normal comparison subjects. Biol Psychiatry 39:703–707.

Gasparotto O C, Ignacio Z M, Lin K, Goncalves S (2002) The effect of different psychological profiles and timings of stress exposure on humoral immune response. Physiol Behav 76:321–326.

Guillemin R, Rosenberg B (1955) Humoral hypothalamic control of anterior pituitary: a study with combined tissue cultures. Endocrinology 57:599–607.

Kostich W A, Chen A, Sperle K, Largent B L (1998) Molecular identification and analysis of a novel human corticotropin-releasing factor (CRF) receptor: the CRF2gamma receptor [In Process Citation]. Mol Endocrinol 12:1077–1085.

Lewis K, Li C, Perrin M H, Blount A, Kunitake K, Donaldson C, Vaughan J, Reyes T M, Gulyas J, Fischer W, Bilezikjian L, Rivier J, Sawchenko P E, Vale W W (2001) Identification of urocortin III, an additional member of the corticotropin-releasing factor (CRF) family with high affinity for the CRF2 receptor. Proc Natl Acad Sci USA 98:7570–7575.

Linton E A, Behan D P, Saphier P W, Lowry P J (1990) Corticotropin-Releasing Hormone (CRF)-BP: Reduction in the Adrenocorticotropin-Releasing Activity of Placental but not Hypothalamic CRF. Journal of Endocrinology and Metabolism 70:1574–1580.

Lovenberg T W, Liaw C W, Grigoriadis D E, Clevenger W, Chalmers D T, De Souza E B, Oltersdorf T (1995)

Cloning and characterization of a functionally distinct corticotropin-releasing factor receptor subtype from rat brain [published erratum appears in Proc Natl Acad Sci USA 1995 Jun. 6;92(12):5759]. Proc Natl Acad Sci USA 92:836–840.

McGaugh J L, Roozendaal B (2002) Role of adrenal stress hormones in forming lasting memories in the brain. Curr Opin Neurobiol 12:205–210.

Mitchell A J (1998) The role of corticotropin releasing factor in depressive illness: a critical review. Neurosci Biobehav Rev 22:635–651.

Nemeroff C B (1989) Clinical Significance of Psycho-neuroendocrinology in Psychiatry: Focus on the Thyroid and Adrenal. J Clin Psychiatry 50:13–20.

Perrin M, Donaldson C, Chen R, Blount A, Berggren T, Bilezikjian L, Sawchenko P, Vale W (1995) Identification of a second corticotropin-releasing factor receptor gene and characterization of a cDNA expressed in heart. Proc Natl Acad Sci USA 92:2969–2973.

Potter E, Behan D P, Fischer W H, Linton E A, Lowry P J, Vale W W (1991) Cloning and characterization of the cDNAs for human and rat corticotropin releasing factor-BPs. Nature 349:423–425.

Reul J M, Holsboer F (2002) Corticotropin-releasing factor receptors 1 and 2 in anxiety and depression. Curr Opin Pharmacol 2:23–33.

Reyes T M, Lewis K, Perrin M H, Kunitake K S, Vaughan J, Arias C A, Hogenesch J B, Gulyas J, Rivier J, Vale W W, Sawchenko P E (2001) Urocortin II: A member of the corticotropin-releasing factor (CRF) neuropeptide family that is selectively bound by type 2 CRF receptors. Proc Natl Acad Sci USA 98:2843–2848.

Sambrook J, Fritsch E F, Maniatis T (1989) Molecular Cloning: A Laboratory Manual, 2nd Edition. Cold Spring Harbor, N.Y.: Cold Spring Harbor Laboratory.

Tache Y, Martinez V, Million M, Wang L (2001) Stress and the gastrointestinal tract III. Stress-related alterations of gut motor function: role of brain corticotropin-releasing factor receptors. Am J Physiol Gastrointest Liver Physiol 280:G173–177.

Takahashi L K (2001) Role of CRF(1) and CRF(2) receptors in fear and anxiety. Neurosci Biobehav Rev 25:627–636.

Takahashi L K, Ho S P, Livanov V, Graciani N, Arneric S P (2001) Antagonism of CRF(2) receptors produces anxiolytic behavior in animal models of anxiety. Brain Res 902:135–142.

Vanitallie T B (2002) Stress: A risk factor for serious illness. Metabolism 51:40–45.

Vaughan J, Donaldson C, Bittencourt J, Perrin M H, Lewis K, Sutton S, Chan R, Turnbull A V, Lovejoy D, Rivier C, et al. (1995) Urocortin, a mammalian neuropeptide related to fish urotensin I and to corticotropin-releasing factor. Nature 378:287–292.

Veith R C, Lewis N, Langohr J I, Murburg M M, Ashleigh E A, Castillo S, Peskind E R, Pascualy M, Bissette G, Nemeroff C B, Raskind M A (1993) Effect of desipramine on cerebrospinal fluid concentrations of corticotropin-releasing factor in human subjects. Psychiatry Res 46:1–8.

Zobel A W, Nickel T, Kunzel H E, Ackl N, Sonntag A, Ising M, Holsboer F (2000) Effects of the high-affinity corticotropin-releasing hormone receptor 1 antagonist R121919 in major depression: the first 20 patients treated. J Psychiatr Res 34:171–181.

---

We claim:

1. An isolated nucleic acid comprising nucleotides 1 to 4917 of SEQ ID NO:1, nucleotides 516 to 4917 of SEQ ID NO:1, nucleotides 1601 to 4917 of SEQ ID NO:1, nucleotides 1947 to 4917 of SEQ ID NO:1, nucleotides 2503 to 4917 of SEQ ID NO:1, nucleotides 3029 to 4917 of SEQ ID NO:1, nucleotides 3532 to 4917 of SEQ ID NO:1, nucleotides 3963 to 4917 of SEQ ID NO:1, or a full length complement of any of the foregoing.

2. An isolated nucleic acid consisting of nucleotides 4868 to 4917 of SEQ ID NO:1.

3. An isolated nucleic acid consisting of nucleotides 4537 to 4917 of SEQ ID NO:1, nucleotides 4647 to 4917 of SEQ ID NO:1, nucleotides 4710 to 4917 of SEQ ID NO:1, nucleotides 4827 to 4917 of SEQ ID NO:1.

4. A nucleic acid comprising a polynucleotide and a heterologous reporter gene operably linked to the polynucleotide wherein the polynucleotide is selected from nucleotides 1 to 4917 of SEQ ID NO:1, nucleotides 516 to 4917 of SEQ ID NO:1, nucleotides 1601 to 4917 of SEQ ID NO:1, nucleotides 1947 to 4917 of SEQ ID NO:1, nucleotides 2503 to 4917 of SEQ ID NO:1, nucleotides 3029 to 4917 of SEQ ID NO:1, nucleotides 3532 to 4917 of SEQ ID NO:1, or nucleotides 3963 to 4917 of SEQ ID NO:1.

5. The nucleic acid of claim 4, wherein the nucleic acid is an expression vector.

6. A host cell comprising the vector of claim 5.

7. A method for determining whether a fragment of (nucleotides 1–4917 of SEQ ID NO:1) that comprises nucleotides 3963 to 4917 of SEQ ID NO:1 is functional under a set of conditions of interest, the method comprising the steps of:
  (a) providing a nucleic acid that comprises the fragment and a heterologous reporter gene operably linked to the fragment;
  (b) subjecting the nucleic acid to the set of conditions of interest;
  (c) measuring the expression level of the reporter gene; and
  (d) comparing the expression level to a suitable control wherein a higher or lower than control expression level indicates that the fragment is functional.

8. A method for screening for an agent that may alter the activity of human CRF-BP promoter, the method comprising the steps of:
  (a) providing a nucleic acid that comprises a polynucleotide and a reporter gene operably linked to the polynucleotide wherein the polynucleotide is selected from nucleotides 1 to 4917 of SEQ ID NO:1, nucleotides 516 to 4917 of SEQ ID NO:1, nucleotides 1601 to 4917 of SEQ ID NO:1, nucleotides 1947 to 4917 of SEQ ID NO:1, nucleotides 2503 to 4917 of SEQ ID NO:1, nucleotides 3029 to 4917 of SEQ ID NO:1, nucleotides 3532 to 4917 of SEQ ID NO:1, or nucleotides 3963 to 4917 of SEQ ID NO:1;
  (b) subjecting the nucleic acid to conditions suitable for the polynucleotide to drive the expression of the reporter gene in the presence of a test agent;
  (c) evaluating the expression of the reporter gene compared to a control nucleic acid that is exposed to the same conditions but without the test agent wherein a higher or lower expression than that of the control nucleic acid indicates that the agent may alter human CRF-BP promoter activity.

9. The method of claim 8, wherein the expression is evaluated at the mRNA level.

10. The method of claim 8, wherein the expression is evaluated at the protein level.

11. The method of claim 8, wherein the nucleic acid is provided in a host cell and wherein the host cell is exposed to the test agent in step (b).

12. A method of determining which region of the human CRF-BP promoter interacts with an agent that is known to alter the activity of the promoter, the method comprising the steps of:
  (a) providing multiple groups of nucleic acids in which a reporter gene is operably linked to a fragment of nucleotides 1–4917 of SEQ ID NO:1, wherein the nucleic acids of the same group contain the same fragment and the nucleic acids in different groups contain different fragments and wherein at least one group contains a fragment that comprises nucleotides 3963 to 4917 of SEQ ID NO:1;
  (b) subjecting the nucleic acids to conditions suitable for the fragments to drive the expression of the reporter gene in the presence of the agent;
  (c) measuring and comparing the reporter gene expression level of each of the nucleic acid groups to that of corresponding controls that are not exposed to the agent to determine the effect of the agent on the promoter activity of different fragments; and
  (d) comparing the effect of the agent on the promoter activity of different fragments.

13. The method of claim 12, wherein the nucleic acids are provided in host cells and wherein the host cells are exposed to the test agent in step (b).

14. A method for screening for an agent that can affect the modulation of the activity of human CRF-BP promoter by cAMP level, the method comprising the steps of:
  (a) providing a host cell that comprises a fragment of nucleotides 1–4917 of SEQ ID NO:1 and a reporter gene operably linked to the fragment wherein the fragment comprises nucleotides 4868 to 4917 of SEQ ID NO:1
  (b) changing the cellular cAMP level;
  (c) exposing the cell to a test agent; and
  (d) determining the expression level of the reporter gene and comparing the expression level to that of a control cell that is not exposed to the test agent wherein a higher or lower than control expression indicates that the test agent can affect the modulation of the human CRF-BP promoter activity by cAMP level.

* * * * *

UNITED STATES PATENT AND TRADEMARK OFFICE
CERTIFICATE OF CORRECTION

PATENT NO.         : 7,122,650 B2                                        Page 1 of 1
APPLICATION NO.    : 10/676526
DATED              : October 17, 2006
INVENTOR(S)        : Patrick H. Roseboom et al.

It is certified that error appears in the above-identified patent and that said Letters Patent is hereby corrected as shown below:

Column 8, line 55, delete "can be used to normalize data".

Column 8, line 56, "expirements" should be --experiments--.

Column 17, Claim 3, line 15, insert --or-- before "nucleotide 4827".

Column 17, Claim 7, line 29, delete "( )" from "(nucleotides 1-4917 of SEQ ID NO:1)".

Column 17, Claim 14, line 49, "ID NO:1" should be -- ID NO:1;--

Signed and Sealed this

Seventh Day of August, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 5001
<212> TYPE: DNA
<213> ORGANISM: Homo sapiens

<400> SEQUENCE: 1
aggcaggtgg atcatttgag gtcagaagtt cgaaaccatc atggccaaca aggtgacacc      60
ccgtctctac taaaaataca aaaattagct gggtgtggtg gtgcacacct gtaatcccag     120
ctactgggga ggctgaggca ggagaattgc ttgaatctgg gaggcagagg ttgcagtgtc     180
ctgagattat gccacagcac tccagcctgg gaaacagagt gagactctgt ctctaaataa     240
ataaataaat aaataaatgc cttctgcaca gcaaaggaaa tgatcaacag ggtgcaaagg     300
taacctacat aatgggagaa aatacttacc aaccatgtat ctgataagtg gttaatatcc     360
aaaatatata agaaactcct acaactcagc aaaaaaccta ttaagtcatt ttaaaaatgg     420
gctaaggact tgaatagaca tttctccaaa gaagacatac aaatggccaa ccagtatatg     480
aaaagatgct caatatcacc aagatcaaga aaatgcaaat caaatccacg acgagacatc     540
acctcgaaac tgttcagatg gctatcatca aaaagataca agatgacaag tgctggcagg     600
gaaaaaagga aaccctggcc actgttagag ggaatggcaa ttagcacagc cattatggaa     660
aacactatgg actttcctca aaaaattaaa atagaggagt attgtatgaa aggagagaag     720
gttaacattc cccttgacaa gaggaacaga aaatcaaata ccgtgtgtcc tcagttataa     780
```

-continued

| | |
|---|---|
| gtgggagcta aatgatgaga acaaacacat ggacacatag agggaaatga cacatactgg | 840 |
| ggcctattgg aagttggagg gtgggaggag ggagaggatc aggaaaaata actgatgggt | 900 |
| actaggctta atacctgggt gaagaaatga tctgtacaac aaacctccat gacacatgtt | 960 |
| tacctatgtg acaaacctgc acatgtactc ctgaagttaa ataaaagtt tttaggccag | 1020 |
| gcacagtggc tcacgcctgt aatcccagca ctttgggagg ccaacgtggg cagatcacga | 1080 |
| ggtcaggaga tcaagaccat cctggctaac acggtgaaac cccgtctcta ctaaacatac | 1140 |
| aaaaaaatta gcctggtgtg gtggcaggcg cctgtagtac cagctactcg ggaggctgag | 1200 |
| acaggagaat ggcgtggacc caggaggcag agcttgcagt gagccaagat catgccactg | 1260 |
| cactccagcc tgggcaacac agcaagactc catctcaaaa aaaaataat gaaaaaataa | 1320 |
| aagttttat aaaaatagaa tggtaatatg attcagcaag cccacttctg cgtatttttc | 1380 |
| caaaagaatt gaaatcagta tgttgaagac atacctgcat tcctatgttc gttgcaccag | 1440 |
| tattcacaat agctaagatg tggaaacaac ctaaatgttg acgaatgaat aaagaaaatg | 1500 |
| tggtatatac atacaatgga atattactca gtctgagaaa agaggaaatc cttgtcatat | 1560 |
| actacagcat ggatgaaact tgaggacatt atgctaagtg aaagatgcca gccacaaaag | 1620 |
| ggcaaatact gtacgattac acttacatga gctatctaaa atagtgagac tcgtagaaga | 1680 |
| agacagtaga atgatggttg cagggattgg gaggagggta aaatggggaa tcgctaataa | 1740 |
| tgggtataaa gtttcagcta tgcaagatga ataagttcca gagatctgtt gtacaacgtt | 1800 |
| gtgcctatag ttgataatat tgtgttgtgc acttaaatat cttttaagag agtagatctc | 1860 |
| gtgttttaac tcttcttacc acaataaaat aaaaataata gctacattca ttcaaacaaa | 1920 |
| tcatcttgaa agcaatggaa aactatttgg tggttgttgt tgttggctaa ctacaatgag | 1980 |
| ttttattcag tagtctttat ttcttaaaga acgcaatgat atgttctatt ttctaacatt | 2040 |
| tcaactaatc gattaatcag gaaaggaaaa aggaagttca tctaaagcat ggattagtga | 2100 |
| tgttctaagt tgacgtgata aataaaagaa aaatttatt atcacaggtc atattacaac | 2160 |
| ttctaacttg cgtgcatagg gattttgtgg tcaccctgaa aacatggcct ataatgtgac | 2220 |
| tgtgaaagcc aagtgcagcc tgtggaggct ctgccatgaa gtgtcagaag ttctctgtgt | 2280 |
| gtgtctcatc agtctaggca caattttaaa ttctgcacct gcccccatgt ccatggattg | 2340 |
| aatatggatc tgctattgtg tggccaccct ggccttcagg cttaacatag gtgacaattt | 2400 |
| gctctgggc tttgtgaaag aaaaaatgtc ttattcctac ctaacaaaaa gaaagtatta | 2460 |
| accctgccta acaatagtcg aagacccaaa aaacaccat ccgggactgt ataacatcaa | 2520 |
| cactggagaa gctatctgga aaatatgga gaaaaactga atatttgaa agtaatggag | 2580 |
| gttaacatac aggtaatttc caatcagcat acttgggac tctgagtttt cccagaacat | 2640 |
| atttaaaaaa aaaatccagt ttgcttgaac aaacaacttt caaatattaa gctaattgtt | 2700 |
| tgaatgacca aagcagtcca tgaaataat ttatcttag tcttcacaca taggcctact | 2760 |
| tattgcccag aaaatttttc ttcggcctaa tccaaattac tcttccattt ctctcaccta | 2820 |
| ttttaatac tttctctcag agagaatggc tacctggctt ctccttgtct tccaatttaa | 2880 |
| tcttcttagt ttttctcgat agcttgtagt ttccatcttt taattaccat taattttttt | 2940 |
| tttttagaa aaggtagttt ccactggctt agtagatatt taccaaactg gtgaaaacta | 3000 |
| cacattaatt tatccaccta gaatttggtg ggaatgaggt ccatcttgta ctataatttg | 3060 |
| tggattaagt aaaatcagat gctatgctat gatgtttgta aaatcagtca ctatgttagt | 3120 |
| gctcattcat cccagctctt gctgtgtgtg gttcctgagg agtgggcatc atgacagcag | 3180 |

-continued

```
ggtgggaaca tcactgttgt ctgtgcacgt gcatgcgtgc atgtgtgtgt gcacatgtgc    3240
acatgtgcat atgcttgtaa aggggctggc tggagaagaa tgtctccttg gtgatgctaa    3300
caaagcaaca ttgagctgga gtgacatcag gtgccagacc ccctaagagg taaaggcaga    3360
ggtctccaag gtgggtgctg gactgaattc tgggaacagg ccaagggctg tggctacatc    3420
aatgggaaag agaagagggc ctgtggcatg cctggtgagt gggcctaagg ctccctctag    3480
gcacaaaaag ggtgggagat agagctgaag atggcctggc atgtttgagg ccagcaagtt    3540
ggggttaagt tgtttgtttt tctcctctttt tattcctccc aggtttcttt ataaccttttt    3600 caaaattcag gcatctaaac agcccttggg atgagaagga catggtggcc agtgtccatg    3660
agctttaggt actcttttcc ctctcactgt ctgtggtctg aggactgctt acaaagttgg    3720
actgtggcac gaaggcctcc tgattaaacc aacaaagagg ccgcctctcc agagctcaga    3780
attgtcctga catgaaaata atcaagttct gacactgcca ggataattac tgtttaattt    3840
cgagtatttt aaaactgaaa atatagccat tccttccttt ataactctgt attatggtct    3900
atttgtaata attgtaataa caatgcttgg tgcagagact ggaaaggggt aggaaagcca    3960
atagtggagc atcctcatgt ttcccacagt ttttggacaca aagaagaaat tctcttctct    4020
cctgataagc agagataagc ttatacttat ttccggatcc ctaagtcatc tttttagccc    4080
tgcaaatttg ctggtgagca gttacaataa agcttcctgg cagttccttc taccagagtg    4140
ttaaagtaat ccaggtattt gaaggcacga atggaatga cttaatctca tctctcagtg    4200
gttcagatgg atgcgaaggt catggctaca gctacctggt ctaggagtgt gtacatcatg    4260
taaacatcca ggtcaagtga cagagctcag ctaaaatcca gaagtcccct gacaccagag    4320
ttagttttcc atgaaagaaa tgcctataag aaactggacc aggataaagc aaagagtaag    4380
gggcaggaag aaagcttata attgcattac tgcaatcttc tgcaaaatca gacttctgct    4440
tctgttccac ctctttaaag ctgaaaatgc ctcaagtttc ttactgagag acatgagaaa    4500
ttccatgaat actaaattct ttgacaattt ctagcatggt ttcatccaag gttatgtgat    4560
gaggctgcat aatataggct ctatatgttt gggtatttta tgcgtgtatg taactttgtc    4620
actttgattt gcaaaatgga aaattccctg aatgcccaca gaaaagtata atgtagcatt    4680
tagcaggtca acaaaatgca ctcccttatt ctttgtctcc gcctcattct ccaacacttt    4740
agtgcactaa gttgtagtga ctgaaatcat tcttggtgaa taatgctggg ccacgctgaa    4800
aatttgtggc tgagagctgg accctcgtca tcgccacgta ctctgtcaat gagacagggt    4860
aacccatggt tactgagctc cgatcagtta aggggcagag agcctccgct ccccactgct    4920
ctataaaaga gacccagcaa agggacccta ccagcttcta gctctcagtc tgcgcgaggg    4980
tgtaggaagg aaagcccagg a                                               5001
```

<210> SEQ ID NO 2
<211> LENGTH: 22
<212> TYPE: DNA
<213> ORGANISM: Artificial
<220> FEATURE:
<223> OTHER INFORMATION: Synthetic PCR primer

<400> SEQUENCE: 2
caccctcgcg cagactgaga gc                                              22